United States Patent [19]

Kawasaki et al.

[11] Patent Number: 4,593,190
[45] Date of Patent: Jun. 3, 1986

[54] APPARATUS FOR INSPECTING CAPSULES

[75] Inventors: Tetsuji Kawasaki; Noriomi Miyoshi; Yukimasa Tachibana, all of Kanagawa, Japan

[73] Assignees: Warner-Lambert K.K., Tokyo; Fuji Electric Company Ltd., Kanagawa; Fuji Elmes Co., Ltd., Tokyo, all of Japan

[21] Appl. No.: 569,984

[22] Filed: Jan. 11, 1984

[30] Foreign Application Priority Data

Jan. 14, 1983 [JP] Japan ................................. 58-4614
Sep. 1, 1983 [JP] Japan ........................... 58-134448[U]

[51] Int. Cl.$^4$ ............................................. G01N 9/04
[52] U.S. Cl. .................................. 250/223 R; 209/522
[58] Field of Search ............... 250/223 R, 223 B, 562, 250/563, 571, 572; 356/445, 446, 448; 209/522, 524, 576, 577, 689, 690, 912

[56] References Cited

U.S. PATENT DOCUMENTS 4,082,188 4/1978 Grimmell et al. ............... 250/223 R
4,158,625 6/1979 Takahashi et al. ............... 250/223 B Primary Examiner—David C. Nelms
Attorney, Agent, or Firm—Frishauf, Holtz, Goodman & Woodward

[57] ABSTRACT

Apparatus for inspecting capsules comprises a carrier belt which is formed into an endless belt configuration and can carry the capsules, with the capsules received separately in through-holes in the belt, and a plurality of parallelly disposed rotatable rollers which have axes of rotation extending substantially in parallel with the flow direction of the capsules being carried by the carrier belt. The rollers rotate the capsules which are in contact therewith. An optical inspecting device is provided for optically inspecting the surfaces of the capsules which are rotated in contact with the rotary rollers. The apparatus can accurately inspect very small defects on the surfaces of the capsules irrespective of the type of capsules, and is simple as well as compact in construction.

14 Claims, 30 Drawing Figures

APPARATUS FOR INSPECTING CAPSULES

BACKGROUND OF THE INVENTION

This invention relates to an apparatus for inspecting defects on surfaces of columnar or cylindrical articles such as medicinal capsules or a machine for sorting empty capsules.

Each medical capsule is composed of a cap and a capsule body, and is formed by combining them. It is necessary that inspection of empty capsules is carried out to detect defects on the surfaces thereof prior to filling them with a drug. With regard to the defects of the capsules, there are well known faults such as holes, cracks, cutoffs and deformations due to which the capsules can be judged to be defective in appearance, and faults such as pinholes of 0.1 mm to 2 mm or so in diameter and thin spots each having a locally thinner wall thickness on the capsule, due to which faults the capsules are scarcely judged to be defective in appearance.

Figure 1A:
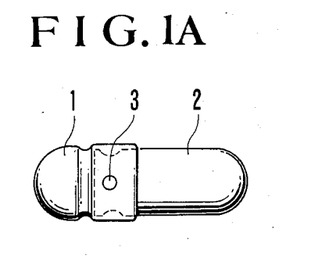
FIGS. 1A and 1B each are an appearance view showing a medicinal capsule.
Figure 1B:
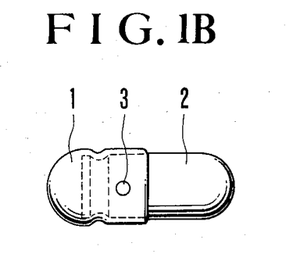
Figure 2:
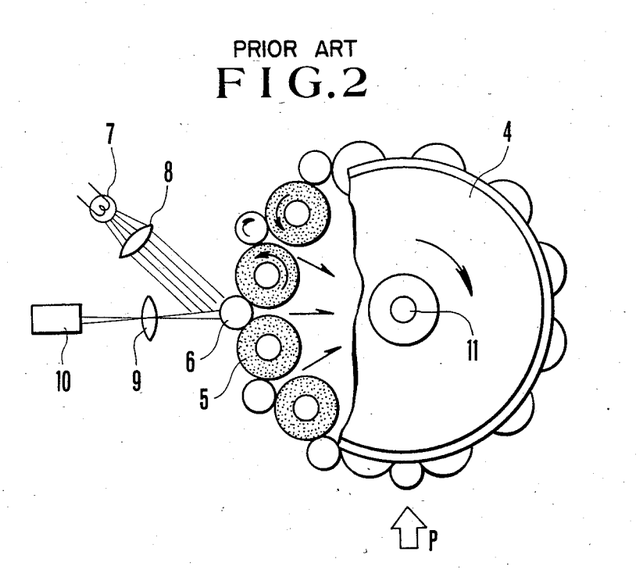
FIG. 2 is a schematic view of a conventional capsule inspecting apparatus.

FIGS. 1A and 1B show a medicinal capsule. The capsule comprises a cap 1 and a body 2, and the cap 1 is provided with a lock hole (notch) 3 for locking it to the body 2. The capsule before packing a drug therein is called an empty capsule, and at this time the combined force between the cap 1 and the body 2 is small. Thus, the empty capsule is, so to speak, in a provisional combined state, as shown in FIG. 1A. After packing the drug, the capsule is in a real combined state, as shown in FIG. 1B in which the combined force between the cap 1 and the body 2 is large due to their being pressed against each other. In the capsules formed like this, a variety of defects will occur thereon sometimes at their manufacture. As the defects, for example, there are a thin spot where a wall thickness of the capsule is partially thin, a hole formed by the build-up of the thin spot, a pinhole, and a chipped cap in which a recess is present on a periphery of the opening of the cap. Further, in the manufactured capsules, defective capsules may be included, and as these defective capsules, there are a loose capsule in which the cap and the body are separated, a twin cap in which the separated cap is recombined with the normal capsule (i.e. non-defective capsule), and a locked capsule in the real combined state into which the empty capsule has been converted in transit. With regard to the medicinal capsules, they are generally classified into opaque capsules and transparent capsules in compliance with the presence and absence of titanium oxide therein, and in some cases, one of the body and the cap of each capsule is transparent and the other thereof is opaque. Therefore, in connection with the inspection of the capsules, a variety of defects mentioned above must be inspected in accordance with such a type of capsules, which fact makes its automation difficult. Hence, it is inevitable at present to rely upon a visual inspection. However, the visual inspection is limited in accuracy. Therefore to replace such a primitive inspection, an inspecting apparatus is now used which is described in Japanese Patent Publication No. 9897/1979 (which corresponds to U.S. Pat. No. 3,709,598) and in which an optical means is employed. The technique disclosed in this patent is as follows:

That is to say, FIG. 2 attached hereto exhibits the principle of the apparatus shown in the aforesaid patent, and in the drawing, reference numeral 4 represents an inspecting head, which has rollers 5 for spinning or rotating capsules disposed on the outer periphery thereof at predetermined intervals and can be rotated intermittently in a clockwise direction, as indicated by an arrow therein, around on a shaft 11. The respective rollers 5 for spinning or rotating the capsules can be rotated at a high speed in an arrow direction by means of a driving mechanism which is not shown. The inspecting head 4 has an air suction mechanism therein which can give suction effect to spaces between the rollers 5 via a suction chamber. The capsules 6 are successively fed in line from a separately disposed capsule feeding mechanism through a position of arrow p to the spaces between the rollers 5. At this time, the capsules 6 are sucked to the spaces therebetween by the air suction mechanism and are held there. Further, when the rollers 5 are rotated, the capsules 6 are correspondingly rotated at about the same speed as that of the rollers.

Figure 3:
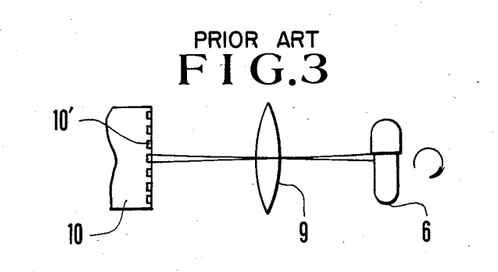
FIG. 3 is a detailed view of the inspecting portion in FIG. 2.

The capsules which are being held and rotated about the inspecting head 4 are subjected to defect inspection in transit thereof. An inspecting section where the defect inspection is carried out is composed of an illuminant lamp 7, an optical lenses 8, 9 and a light sensor 10. The light radiated from the illuminant lamp 7 reaches the surfaces of the capsules through the optical lens 8 in the form of a lengthwise strip belt and is hit along an axis of each capsule 6. The reflected light from the capsule 6 is reached to the light sensor 10 through the optical lens 9. FIG. 3 illustrates schematically the aspect in which the reflected light from the capsule 6 reaches the light sensor 10. The light sensor 10 is provided, on the light-receiving surface thereof, with a plurality of photocells 10' in parallel. The light which reaches the respective photocells 10' contains information about different parts on each capsule 6. Accordingly, defects on the surface of the capsule 6 can be inspected by measuring an output from each photocell 10'.

This inspecting apparatus permits automatic inspection of defects on the surface of the capsules and is more excellent than the visual inspection by inspectors. However, in the case that the inspection of very small faults such as pinholes is carried out, the above inspecting apparatus requires several tens of the photocells 10'. For example, when a pinhole of 0.5 mm in diameter on the capsule of 20 mm in length is detected, the photocells as many as 40 are required. Although each photocell is not so expensive, many photocells having similar characteristics must be arranged and much attention must be paid to their maintenance, because unless the characteristics of the respective photocells are the same, accurate inspection cannot be accomplished. Moreover, the increase in the number of the photocells correspondingly leads to an increase in judging circuits, and the apparatus becomes expensive.

An object of this invention is thus to provide an apparatus for inspecting faults on capsules, which apparatus can overcome the aforementioned drawbacks of the conventional technique, can inspect accurately very small defects on the surfaces of the capsules irrespective of a type of capsules, and is simple as well as compact in constitution.

SUMMARY OF THE INVENTION

The above-mentioned object can be accomplished, according to this invention, by an apparatus for inspecting capsules comprising a carrier belt or conveying belt which has an endless belt configuration, can be moved rotatively in a predetermined rotary direction corresponding to a lengthwise direction thereof, has at least one row of through-holes provided along the rotary direction, and can carry the capsules, with these capsules received separately in through-holes in the belt; a plurality of parallelly disposed rotary rollers which have rotary axes extending substantially parallel with the flow direction of the capsules and are brought into contact with the capsules being carried by the carrier belt in order to rotate the capsules about the rotary axes thereof; and an optical inspecting device for inspecting optically the surfaces of the capsules being rotated in contact with the rotary rollers.

In the present invention, the apparatus may comprise a first inspecting member for mainly inspecting opaque portions and a second inspecting member for mainly inspecting transparent portions of the capsules, the inspecting members are being disposed in a predetermined locational relation in a conveying direction of the capsules, and the type check of the capsules as well as the defect inspection on the opaque portions is primarily carried out by means of the first inspecting member and the defect inspection on the transparent poritons is then carried out by means of the second inspecting member, whereby defects on the capsules can be inspected with high accuracy irrespective of a type of capsules.

BRIEF DESCRIPTION OF THE DRAWINGS

FIGS. 7A, 7B and 7C show a carrier belt in FIG. 6, where

DESCRIPTIONS OF THE PREFERRED EMBODIMENTS

Now, this invention will be described in detail by way of an embodiment with reference to the accompanying drawings.

Figure 4:
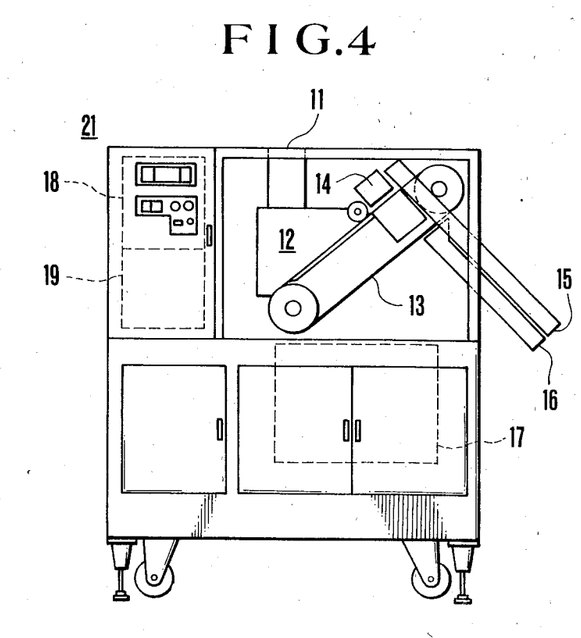
FIG. 4 is a schematic elevational view of one embodiment of this invention.
Figure 5:
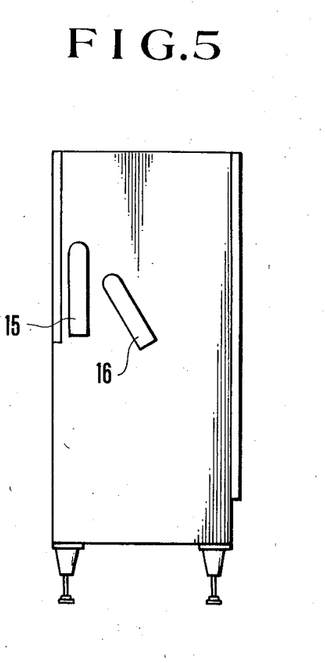
FIG. 5 is a schematic side view of FIG. 4.

The embodiment of this invention will be described in outline in accordance with FIGS. 4 and 5.

Capsule are quantitatively fed to a feed inlet 11 of the apparatus body 21 by an outer capsule feeding device, and are transferred to a carrier belt 13 in a feed chamber 12. The capsules which are being carried separately in line by the carrier belt 13 are subjected to inspection on the surfaces thereof by an optical inspecting device 14, and output signals from the inspecting device 14 are transmitted to a judging control section 17 where quality of the capsule is judged. The capsules which have been inspected are classified into defective products and normal products and are discharged into a chute 16 for the defective products and a chute 15 for the normal products, respectively. Furthermore, the apparatus body 21 is provided with an operation board (panel) 18 thereon and a setting display board (panel) 19 therein. The operation board 18 comprises pilot lamps for indicating ON or OFF of a power source and operating conditions, switches for starting and stopping the apparatus as well as for setting a kind (the whole capsule body is transparent or opaque, either one of the cap or the body is transparent and the other is opaque, or the like) of capsules to be inspected, and counters for counting sorted capsules. Further, the setting display board 19 comprises switches for setting an operating mode, an inspection accuracy and a light volume level of the inspecting device, and pilot lamps for indicating operating conditions of various members and results of capsule inspection.

Now, constitutional elements in one embodiment shown in FIG. 6 will be described in detail.

Figure 6:
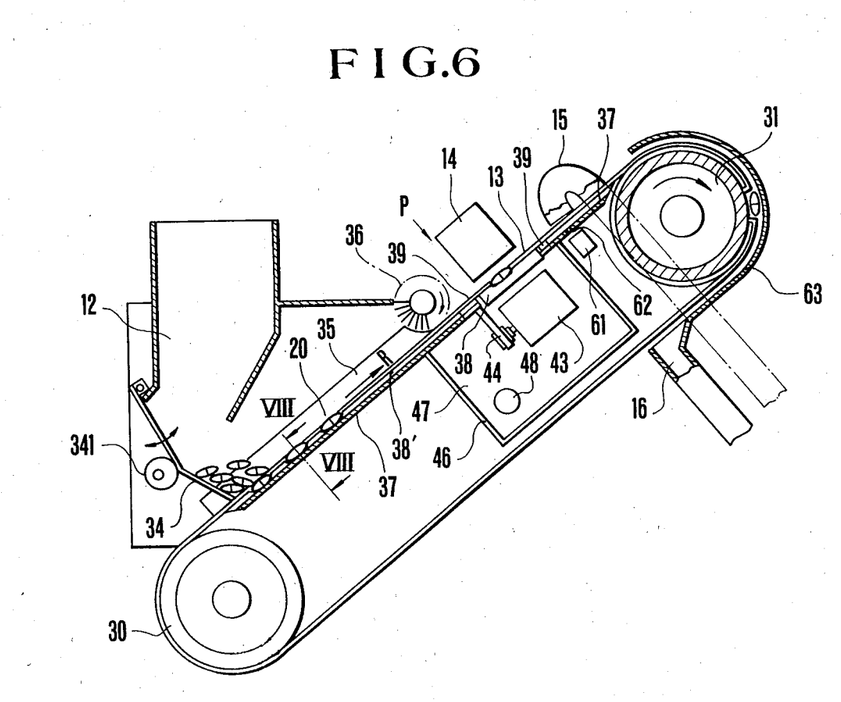
FIG. 6 is an enlarged view illustrating the principal part of one embodiment of this invention.
Figures 7A, 7C:
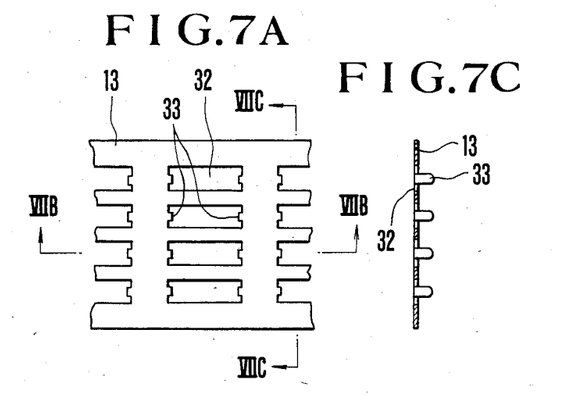
FIG. 7A is a partial enlarged view.
FIG. 7C is a sectional view taken along line VIIC—VIIC in FIG. 7A.
Figure 7B:
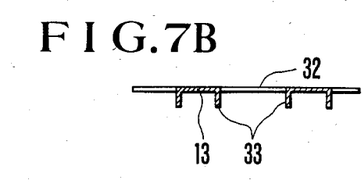
FIG. 7B is a sectional view taken along line VIIB—VIIB in FIG. 7A.
Figure 8:
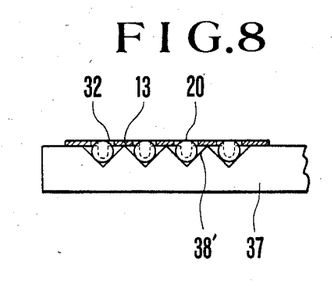
FIG. 8 is a sectional view taken along line VIII—VIII in FIG. 6.
Figure 9:
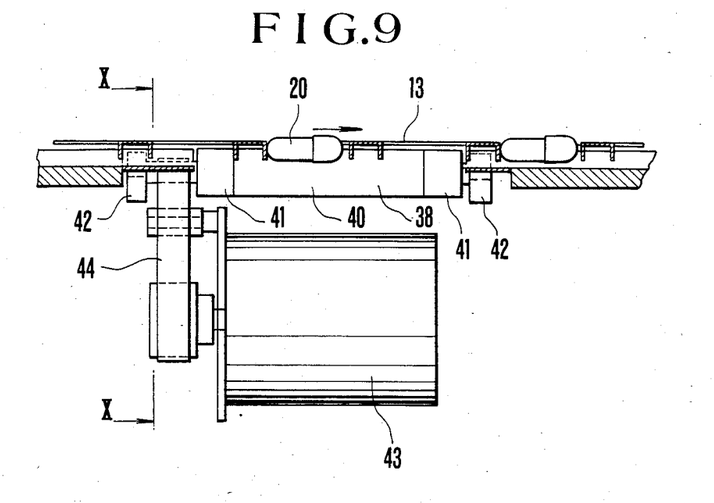
FIG. 9 is an enlarged view of the rotary roller portion in FIG. 6.
Figure 10:
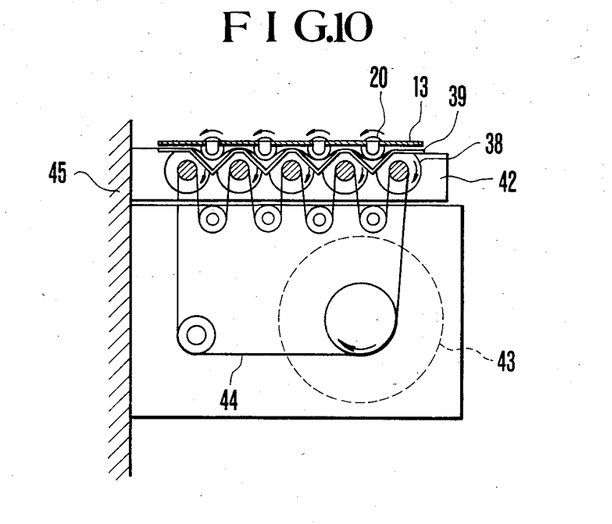
FIG. 10 is a sectional view taken along line X—X in FIG. 9.

As exhibited in detail in FIG. 6, the carrier belt 13 extends between a pulley 30 and another pulley 31 disposed obliquely above the pulley 30 and is rotated in an arrow direction R by means of a suitable rotary drive machine. As FIG. 7 shows, the carrier belt 13 is made of a metal and is provided, on the outer peripheral surface thereof, with through-holes 32 at equal intervals. Each through-hole 32 is adapted to receive a capsule separately so that the lengthwise direction of the capsule may be in parallel with the running direction of the carrier belt. On the opposite lengthwise sides of each through-holes 32, there are provided lugs 33. The through-holes 32 are formed so as to be arranged in four rows on the carrier belt 13. Here, the description will be continued returning to FIG. 6 again. In the feed chamber 12 in which the capsules are stored for a moment and are surely received in the through-holes 32 on the carrier belt 13, there are disposed a rocking plate 34 for rocking suitably the momentarily kept capsules in order to prevent them from overlying each other and from clogging the through-holes, an orienting plate 35 for orienting the capsules so that the lengthwise direction thereof may be in parallel with a flow direction thereof, and a brush 36 for returning, to the feed chamber 12, the capsules which are not received in the through-holes 32 on the carrier belt 13 or are disordered even though received therein. The rocking plate 34 can be rocked by a rocking means, e.g. an eccectric roller 341. The capsules 20 received in the through-holes 32 of the carrier belt 13 are supported on the undersides thereof by V-shaped grooves 38' provided on a guide plate 37 and are carried sliding on the V-shaped grooves 38' of the guide plate 37 (see FIG. 8). At an end of the guide plate 37 which confronts the rotary rollers 38, there is a plate 39, which is made of a material having a good wear resistance and a low friction coefficient and is easy to change. As seen from FIGS. 9 and 10, the rotary axes of rotary rollers 38 are substantially in parallel with the lengthwise axes of the capsules 20 being carried by the carrier belt 13. One line of the capsules 20 is in contact with the two adjacent rotary rollers 38 and the former 20 are rotated at a high speed by the latter 38. The rotary rollers 38 have their outer surface central portions 40 made of a rubber and their opposite end portions 41 made of a material having a good wear resistance and a low friction coefficient. Shafts of the rotary rollers 38 are supported by a support 42 secured to the base plates 45, and mechanical power from a motor 43 is transmitted to the rotary rollers 38 via a belt 44, whereby the rotary rollers 38 all are rotated in one direction. The rotary rollers 38 lie in a suction chamber 47 defined by a wall 46 (see FIG. 6). The suction chamber 47 is maintained in a negative-pressure state by vacuuming through an air-inhaling opening 48, and sucks the capsules so as to settle each of them between the two adjacent rotary rollers 38. As a result, no slide motions exists between the capsules and the rotary rollers 38, and rotation movement of the rotary rollers 38 can be surely transmitted to the capsules. Further, since the capsules are rotated while settled between the two adjacent rotary rollers 38 by the suction based on the aforesaid negative pressure, the capsules can be smoothly and stably rotated with less vibration, and since the capsules are rotated without contact with the carrier belt 13, there is no fear that they are hurt and damaged.

Figure 11:
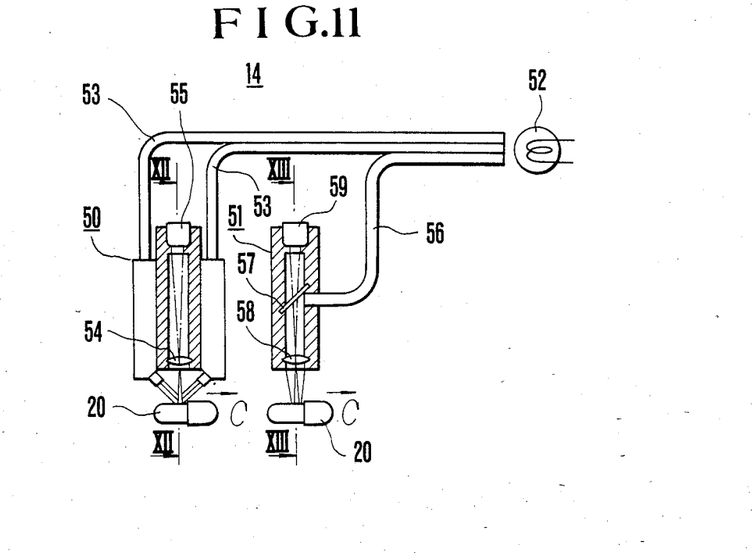
FIG. 11 is an enlarged view of the optical inspection portion in FIG. 6.
Figure 12:
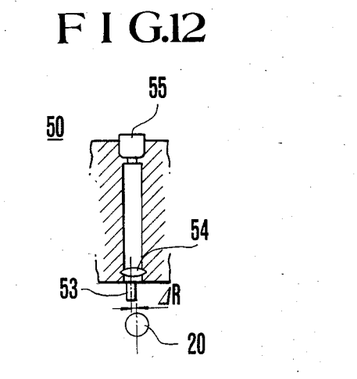
FIG. 12 is a sectional view taken along line XII—XII in FIG. 11.
Figure 13:
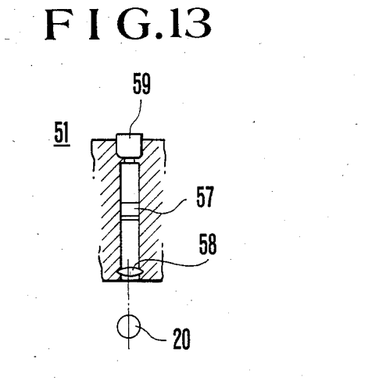
FIG. 13 is a sectional view taken along line XIII—XIII in FIG. 11.
Figure 14:
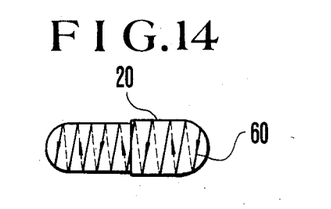
FIG. 14 shows a capsule on which a scanning route taken by an inspecting device is indicated.

FIG. 11 attached hereto illustrates an optical inspeciton device for inspection the capsule surfaces rotating in contact with the rotary rollers 38. This optical inspecting device 14 comprises an inspecting member 50 for inspecting mainly the opaque capsules and an inspecting member 51 for inspecting mainly the transparent capsules. The inspecting member 50 comprises an illumination system comprising an illuminant lamp 52 and an optical fiber 53 for guiding the light from this lamp to the capsule surfaces, and a light sensor system adapted to impinge the reflected light from the capsule surfaces against a light sensor 55. The inspecting member 51 comprises an illumination system including an optical fiber 56 for guiding the light from the lamp 52 to the capsule surfaces and a half mirror 57, and a light sensor system adapted to impinge the reflected light from the capsule surfaces against a light sensor 59 via a magnifying lens and the half mirror. These inspecting members 50 and 51 are disposed so as to face to the respective rows of the through-holes 32 on the carrier belt 13. The position relations between each of the inspecting members 50 and 51 and the capsules on each row are shown in FIGS. 12 and 13. The inspecting member 50 is disposed deviating slightly from the axis of rotation of each capsule 20 by ΔR, whereby the inspecting member 50 can observe a diffusively reflected light from the capsule surfaces. On the other hand, the inspecting member 51 is disposed in a plane passing through the axis of rotation of each capsule 20, whereby the inspecting member 51 can observe a directly reflected light from the capsule surfaces. As a result of the fact that the capsules are rotated about the axes thereof at a high speed by the rotary rollers 38 while carried by the carrier belt 13 in the lengthwise direction thereof, the capsule surfaces can be scanned by the light sensors 55 and 59 as shown in FIG. 14. That is to say, as understood from the scanning route represented by reference numeral 60 along which the light sensors 55 and 59 scan, the capsule surfaces are helically scanned, whereby each capsule can be scanned all over the surface thereof. The smallest sizes S (scaning pitch) of faults on the capsules which can be inspected is decided by the following formula:

$$S = \frac{V}{n \cdot N}$$

wherein
V: Flow velocity of the capsules,
n: Number of the light sensors, and
N: Rotation frequency of the capsules.

In this embodiment, there are set conditions that the number of the light sensors is one, the flow velocity of the capsules 20 is 200 mm/s, and the rotation rate of the capsules 20 is 30,000 rpm, so that defects of approximately 0.4 mm or more in diameter can be detected.

Reference will be made hereinafter to the judging control section 17 for judging quality of the capsules on the basis of the output from the light sensors 55 and 59.

The capsules 20 which have undergone the inspection by the optical inspecting device 14 are forwarded to a discharge section. A defective capsule discharge section comprises a nozzle 61 for jetting air from the inside of the carrier belt 13 toward the outside thereof and a defective capsule discharge chute 15 (see FIG. 6). Thus, in the defective capsule discharge section, air jetted from the nozzle 61 hits against the capsules through openings 62 of the guide plate 37, and the jetted air is controlled by a suitable solenoid valve which is not shown. A normal capsule discharge section includes a normal capsule discharge chute 16, and in the normal capsule discharge section, the capsules are dropped by gravity thereof.

Now, the successive flow of the capsules will be described:

The capsules 20 which are stored for a moment in the feed chamber 12 are received in the through-holes 32 on the carrier belt 13 which is driven in an arrow direction in FIG. 6, and are then carried by the carrier belt 13, sliding on the V-shaped grooves 38' on the guide plate 37 disposed inside the carrier belt 13. When the capsules being carried, sliding on the guide plate 37 are transferred to the rotary roller 38 at the end portion of the guide plate 37, the capsules are sucked toward the suction chamber 47 to be settled on the rotary rollers 38 which is being rotated at a high speed. In consequence, the capsules are rotated at a high speed by the rotary rollers 38 while carried by the carrier belt 13, and the capsules surfaces are scanned helically by the optical inspecting device 14. The capsules which have undergone the inspection by the optical inspecting device 14 are further carried by the carrier belt 13 and are then transferred from the rotary rollers 38 to the guide plate 37, and then to the defective capsule discharge section. Some capsules which are defective are discharged into the defective capsule discharge chute 15 by compressed air through the nozzle 61, when having arrived at the position of the defective discharge chute 15. The other capsules which are normal are further carried by the carrier belt 13 and are then transferred from the guide plate 37 to the pulley 31, and they are forwarded, while sustained by an outer guide plate 63, to the normal discharge section. The capsules which have reached this section are discharged into the normal capsule discharge chute 16 by gravity. The capsules discharged through the respective chutes 15 and 16 are collected in storing boxes, respectively.

The oblique angle of the carrier belt 13 is such that the capsules can be received in the through-holes 32 of the carrier belt 13 in the feed chamber 12 at a high probability and the capsules which are not received in the through-holes 32 or are disordered even though received therein can be easily returned to the feed chamber by the brush 36. Suitably, the oblique angle ranges from 40° to 45° with respect to a horizontal plane.

Next, reference will be made to the judging control section 17 for judging defects on the capsules by scanning their surfaces helically in accordance with the optical inspection technique.

Figure 15:
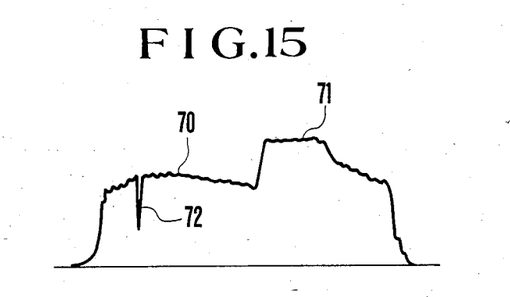
FIG. 15 is an output waveform obtained by an inspecting member 50 in FIG. 11.
Figure 16:
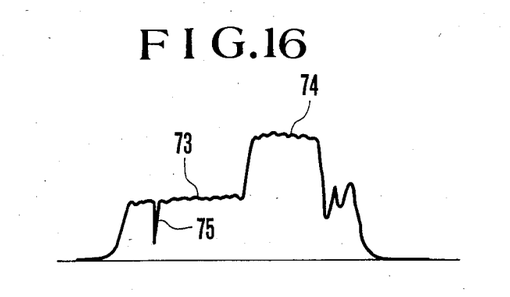
FIG. 16 is an output waveform obtained by an inspecting member 51 in FIG. 11.

FIGS. 15 and 16 show output waveforms obtained by the light sensors 55 and 59 in the case that there is a pinhole of 0.5 mm or so in diameter on the surface of the capsule. FIG. 15 exhibits an output waveform obtained by the light sensor 55 at the time when the capsule was opaque and was inspected by the inspecting member 50. In this drawing, reference numerals 70, 71 and 72 mean reflected lights from the capsule body, its cap and the pinhole on the capsule surface, respectively. FIG. 16 exhibits an output waveform obtained by the light sensor 59 in the case where the capsule was transparent and was inspected by the inspecting member 51. In this drawing, reference numerals 73, 74 and 75 mean reflected lights from the capsule body, its cap and the pinhole on the capsule surface, respectively. As understood from these drawings, a change in the reflected light means the pinhole on the capsule surface definitely appears irrespective of the capsule being opaque or transparent.

Figure 17:
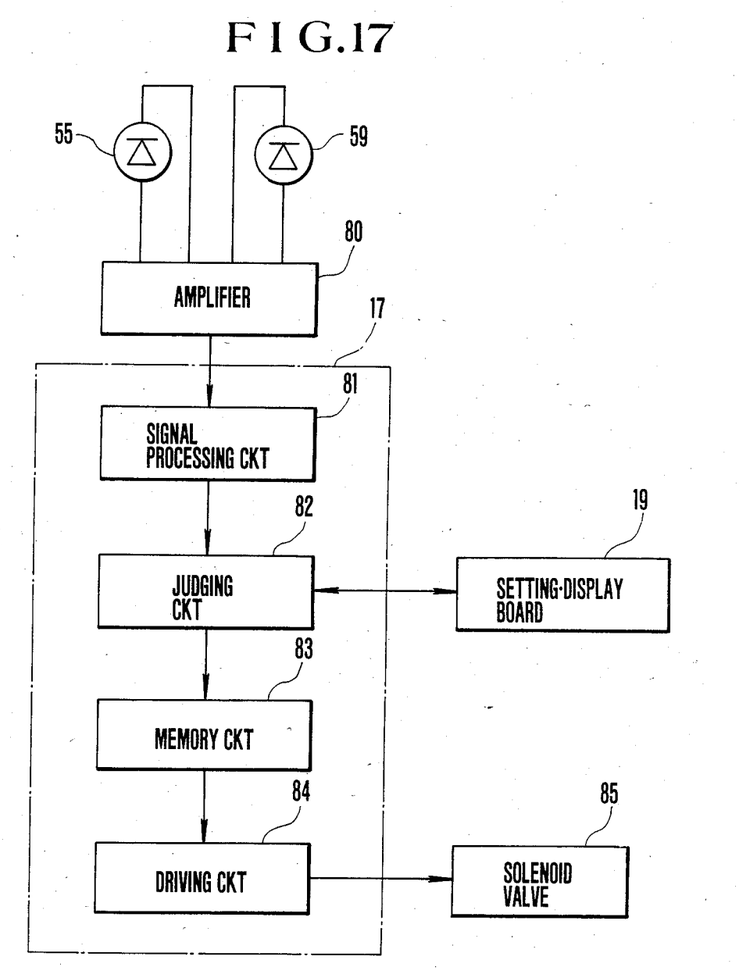
FIG. 17 is a block diagram for a judging control portion.
Figure 18A:
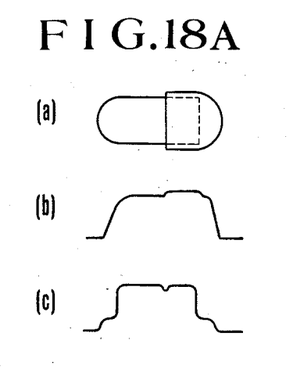
FIGS. 18A, 18B, 18C and 18D show output waveforms from the respective inspecting members in the instance where the capsules to be inspected are lock capsules.
Figure 18B:
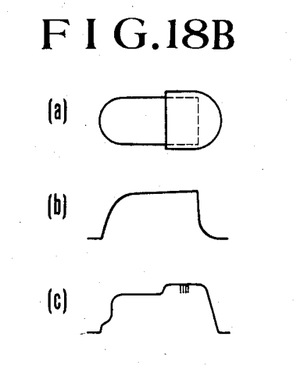
Figure 18C:
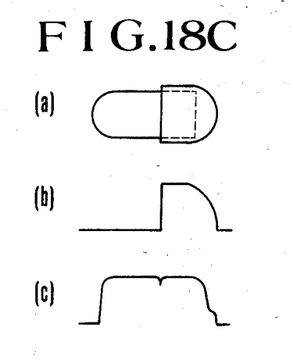
Figure 18D:
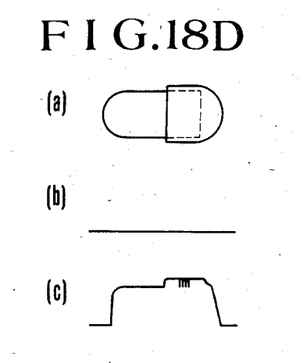

FIG. 17 shows a block diagram of the judging control section 17. In this drawing, photoelectric signals from the light sensors 55 and 59 are amplified by an amplifier 80, and are then transmitted to the judging control section 17. This judging control section 17 is composed of a signal processing circuit 81, an judging circuit 82, a memory circuit 83 and a driving circuit 84. In the signal processing circuit 81, among output signals from the amplifier 80, direct-current components are removed to unify a signal level for defects, and output signals and set thresholds are compared with each other in compliance with a set inspection accuracy on the setting display board to produce two-valued signals. In the judging circuit 82, the output signals from the signalprocessing circuit 81 are observed totally about a kind of capsules and defective items in order to judge as to whether they are defective or normal. Results judged at the judging circuit 82 are stored for a moment in the memory circuit 83. The results stored temporarily are read out when the capsules which have undergone the quality judgement are carried and reach the defective product discharge section by means of the carrier belt 13, and the above signals are then transmitted to the driving circuit 84. In compliance with the results, the driving circuit 84 controls, in the case that the capsule is defective, the solenoid valve 85 for detective product discharge. Results of the judgement by the judging circuit 82 are indicated on the setting display board 19.

Next, reference will be made to how defects such as the locked capsule, twin cap and hole are judged in a judging control section 17 in compliance with a type of capsules.

FIGS. 18A to 18D are illustrative views showing relations between the capsules to be inspected and output waveforms obtained from the inspecting members 50 and 51. In terms of a relation of the body to the cap of each capsule, i.e. a body/cap relation, FIGS. 18A, 18B, 18C and 18D exhibit cases of an opaque (OP)-/opaque (OP), an opaque (OP)/transparent (TR), a transparent (TR)/opaque (OP) and a transparent (TR)/transparent (TR) relation, respectively. In other words, according to the type of capsules, there are four cases of FIGS. 18A to 18D. For the respective cases, output waveforms (b) and (c) can be obtained from the inspecting members 50 and 51, respectively. Therefore, the judgement of the defects can be accomplished on the basis of these output waveforms. For example, since the output waveforms from the inspecting member 50 vary with the types of the capsules (OP/OP, OP/TR, TR/OP and TR/TR), the inspection of the output waveforms will permit at least a type of capsule to be known. Further, mutually varied waveforms can likewise be obtained from the inspecting member 51 in accordance with the types of capsules. In this case, when a length of each capsule is inspected from a width of the obtained output waveforms and a check is made as to whether the obtained value is within the range of standard values representing the empty capsule, the locked capsule which is generally shorter than the normal one can be discriminated.

Figure 19A:
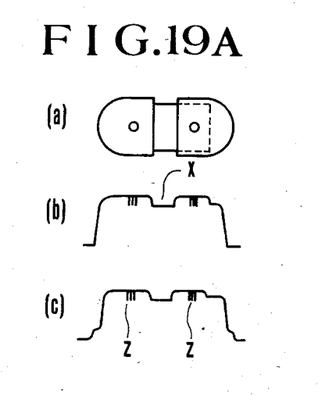
FIGS. 19A and 19B show output waveforms from the respective inspecting members in the instance where the capsules to be inspected are twin cap capsules.
Figure 19B:
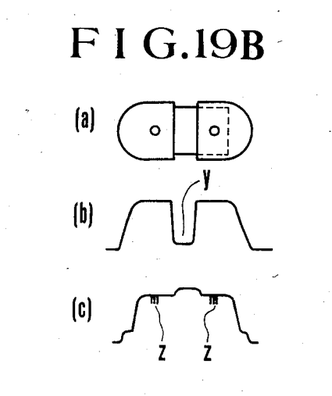

FIGS. 19A and 19B are illustrative views showing the twin cap capsules. Of these drawings, FIG. 19A is directed to the instance where the body/cap relation is opaque/opaque, and FIG. 19B is about the instance where it is transparent/opaque.

Also in the case of the twin cap capsules, a type of capsules is likewise judged by means of the inspecting member 50, and since such a step portion x as in FIG. 19A (b) or such a recess portion y as in FIG. 19B (b) appears at this time, the twin cap capsules can be instantaneously discriminated by them. As in FIG. 19A, however, when the capsule is nearly transparent, such a discrimination will be infeasible. On the other hand, in the inspecting member 51, two signals z based on the notches shown in FIG. 1 are obtained as elucidated in FIGS. 19A and 19B, and they permit distinguishing the twin cap capsules.

Figure 20A:
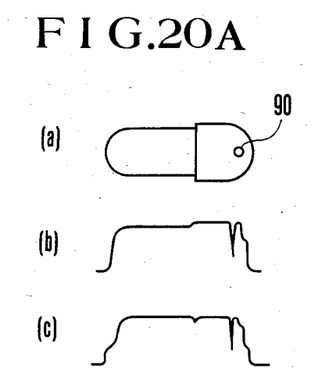
FIGS. 20A and 20B show output waveforms from the respective inspecting members in the instance where the capsules to be inspected have holes.
Figure 20B:
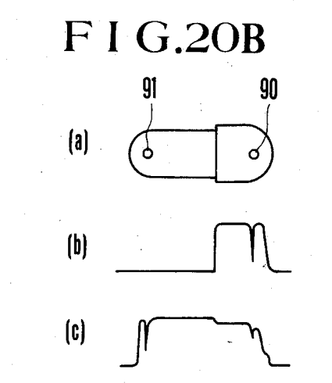

FIGS. 20A and 20B are illustrative views showing the holed capsules. Of these drawings, FIG. 20A is directed to the instance where the body/cap relation is opaque/opaque, and FIG. 20B is about the instance where it is transparent/opaque.

When the opaque/opaque capsule has a hole 90 as shown in FIGS. 20A (a), a good inspection can be accomplished by both of the inspecting members 50 and 51, as shown in FIGS. 20A (b) and 20A (c). On the other hand, when holes 90 and 91 are present on both the transparent and opaque portions of the transparent/opaque capsule as shown in FIG. 20B, the inspection of the hole 91 on the opaque portion is carried out by the inspecting member 50 as shown in FIG. 20B (b), and the inspection of the holes 91 on the transparent portion is done by the inspecting member 51 as shown in FIG. 20B (c).

Next, reference will be made to a judging operation in the instance where the body/cap relation of the capsule is opaque/opaque, in accordance with FIG. 21. Prior to this judgement operation, the switch mounted on the operation board 18 is set to the condition that the body and the cap are opaque.

In the first place, it is checked at a step A whether or not the body/cap relation of the capsules to be inspected are coincident with the setting condition. The inspected result is judged (step B), and if the setting is right, a twin inspection (I) is carried out, as already described regarding FIG. 19A (step C). After the check result has been judged (step D), a hole inspection is carried out as described regarding FIG. 18A (step E), and the inspected result is judged (step F). If the result is good, a lock inspection is then carried out (step G) as described regarding FIG. 18A, and the inspected result is judged (step H). If the result is good, the twin inspection (II) is afterward carried out again (step I), and its result is judged (step J). The capsules in which all of these judged results are good are normal capsules, and the capsules having even one bad result are sorted out as defective capsules. As be definite from the foregoing, the inspections on the steps A, C and E are accomplished exclusively by the inspecting member 50, and the inspections on the steps G and I are accomplished mainly by the inspecting member 51. The reason why the twin inspection is carried out twice is that when the capsule is nearly transparent, the inspeciton by the inspecting member 50 is infeasible.

Figure 22:
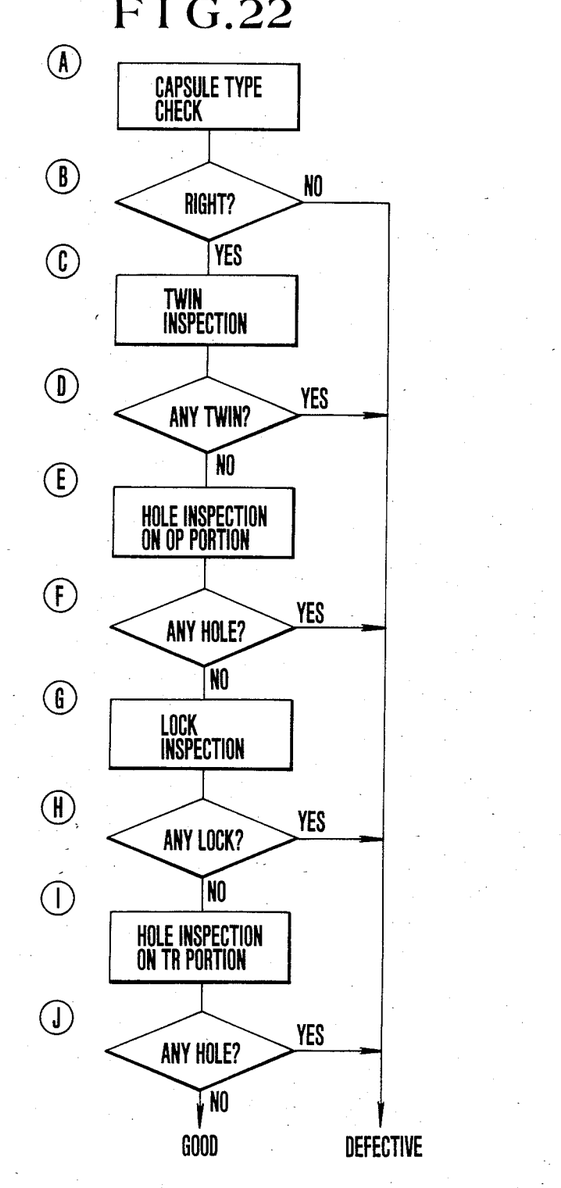

Next, reference will be made to a judging operation in the instance where the body/cap relation of the capsule is transparent/opaque, in accordance with FIG. 22. Also in this case, needless to say, the condition of the body/cap relation is first set to a transparent/opaque designation.

Figure 21:
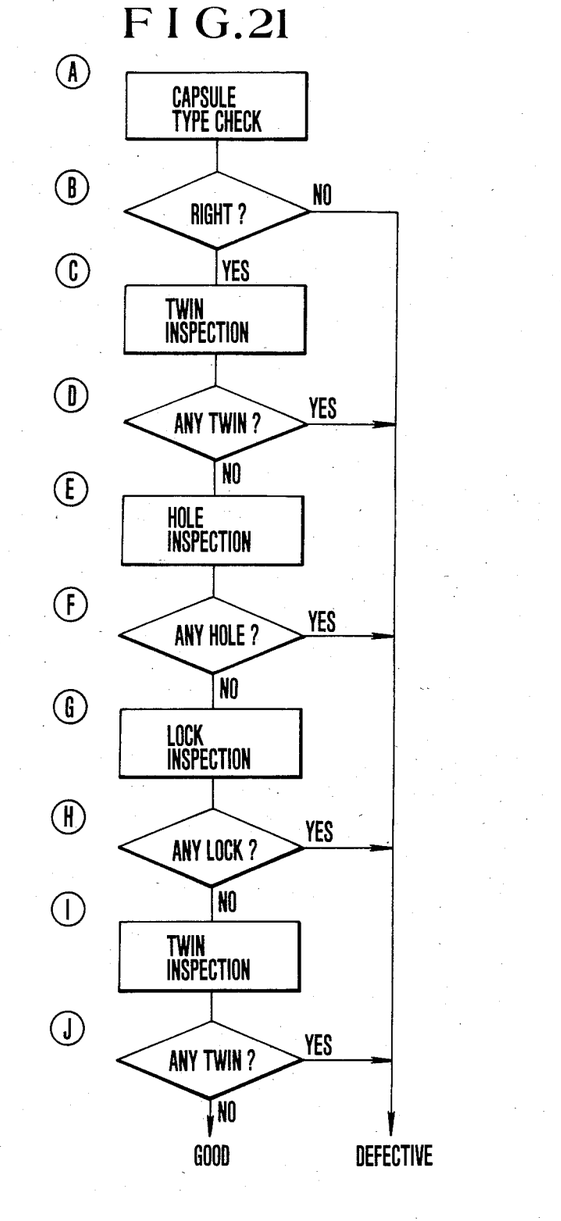
FIG. 21 and 22 each are a flow chart showing a defect inspecting operation in the instance where the body/cap relations of the capsules are opaque/opaque and transparent/opaque, respectively.

This judging operation is characteristically carried out by separating the hole inspection into an inspection on the transparent portion (TR) and an inspection on the opaque portion (OP) (steps E and I), and the other inspection steps are the same as in the case of FIG. 21. The reason why such a procedure is taken will be clear from the descriptions regarding FIGS. 19B and 20B; therefore a further explanation is omitted here.

In the above, the description has been made in the instance where the defect is the lock, twin cap or hole, and the body/cap of each capsule is opaque/opaque or transparent/opaque. However, also in the instance where the capsule is opaque/transparent or transparent/transparent and the defect is the thin spot, the inspection can be accomplished in the same manner as described above. Further, the above described inspections can be applied to not only the aforesaid medicinal capsules but also to similar columnar or cylindrical articles.

According to this invention, the capsules in each row are rotated about the axes thereof by the two adjacent rotary rollers while carried by the carrier belt in the lengthwise direction thereof, whereby the whole surfaces of the capsules can be scanned spirally. Accordingly, the following functional effects can be obtained:

(1) The surfaces of the capsules which are stably rotated at a high speed can be scanned spirally. Therefore, fine defects can be detected all over the surfaces of the capsules by one or plural light sensors. This can simplify noticeably a detecting system and a detecting circuit for the signal processing of a two-dimensional image by an industrial television camera or the like.

(2) Since the capsules are sucked from between two adjacent rotary rollers and are rotated in contact with them while carried by the carrier belt, the rotation of these capsules can be accomplished smoothly with less vibration irrespective of size thereof, and the accuracy of the defect inspection can be improved.

(3) In each capsule being rotated in contact with the rotary rollers, its rear end is spherical and is in contact with the carrier belt at one point on the rotary axis of the capsule. Therefore, the rotation of the capsules is not hindered. Further, since the front end of each capsule is not brought into contact with the carrier belt, the capsule surfaces are not hurt and damaged.

(4) The capsules can be carried without restricting their orientation to a predetermined direction, e.g. without orienting their caps. Therefore the structure of the carrier mechanism is extremely simple and its manufacturing cost can be reduced.

(5) The flow speed and the rotary speed of the capsules can be independently regulated, and a resolving power (size of defects to be detected) can be very easily altered.

(6) Since the capsules become parallel with the lengthwise axes of the through-holes on the carrier belt in the feed section, a probability of the capsules being received in the through-holes can be easily heightened.

(7) The carrier belt is obliquely disposed and the capsules are carried from a lower position to a higher position. Therefore, the capsule which are not received in the through-holes on the carrier belt in the feed chamber and which are disordered and confused even though received therein can be readily returned to the feed chamber.

(8) The whole structure is extremely simple and its maintenance and check can be easily carried out.

(9) Often appearing defects such as the locked capsules, twin caps and holes can be inspected with high accuracy irrespective of a type of capsules by organically utilizing the mechanisms of the disposed first inspecting member for mainly inspecting the opaque portions and the second inspecting member for mainly inspecting the transparent portions of the capsules. Hence, it is sure that device is extremely high in the practical effect.

we claim:

1. An apparatus for inspecting capsules, comprising: and endless belt;

means for rotatingly driving said endless belt in a predetermined rotary direction corresponding to a lengthwise direction of said endless belt;

said endless belt having at least one row of through-holes provided therein along said rotary direction for receiving capsules to be inspected, with the capsules being separately received in said through-holes;

said capsules, received in said through-holes being carried by said endless belt and being moved by said rotatingly driven endless belt in a given flow direction;

a plurality of parrallelly disposed rotary rollers having rotary axes extending substantially in parallel with said flow direction of said capsules and which are arranged to contact with the capsules being carried by said endless belt in order to rotate said capsules about axes of rotation thereof; and and optical inspecting device for optically inspecting the surface of said capsules being rotated in contact with said rotary rollers.

2. the apparatus of claim 1, wherein said endless belt has lugs for supporting said capsules at opposite lengthwise ends of each of said through-holes.

3. The apparatus of claim 2, wherein said endless belt is obliquely disposed so as to carry said capsules from a lower position side to a higher position side which is higher than said lower position side.

4. The apparatus of claim 3, comprising: means for transferring said capsules to said endless belt on said lower position side; and said transferring means including a rocking plate at said lower position side for providing said capsules being transferred with a rocking motion.

5. Ths apparatus of claim 4, wherein said transferring means includes a feed chamber at said lower position side.

6. The apparatus of claim 5, comprising a brush at said higher position side of said carrier belt for returning to said feed chamber at said lower position side of said endless belt, capsules which are not received in said through-holes of said endless belt and capsules which are disordered even though received in said through-holes.

7. The apparatus of claim 6, wherein said rotary rollers have elastic outer peripheral surfaces, and have opposite end portions which are made of a material having a wear resistance and a friction coefficient which is lower than that of said elastic outer peripheral surfaces of said rollers.

8. The apparatus of claim 7, comprising rotating means for rotating said rotary rollers, said rotating means including one driving motor and one belt coupled to said one motor, said one belt being connected to said rotary rollers.

9. The apparatus of claim 1, wherein said inspecting device comprises:
a first optical inspecting member for inspecting mainly opaque capsules; and
a second optical inspecting member for inspecting mainly transparent capsules.

10. The apparatus of claim 9, wherein said first optical inspecting member for inspecting mainly opaque capsules comprises:

an illumination system including an optical fiber system for guiding light from and illumination lamp to the surfaces of said capsules; and
a light sensor system for receiving and impinging reflected light from the surfaces of said capsules against a light sensor.

11. The apparatus of claim 9, wherein said second optical inspecting member for inspecting mainly transparent capsules comprises:
and illumination system including an optical fiber for guiding light from an illumination lamp to the surfaces of said capsules through a half mirror; and
a light sensor system for receiving and passing reflected light from the surfaces of said capsules through a magnifying lens and said half mirror and then to a light sensor.

12. The apparatus of claim 9, wherein said first optical inspecting member for inspecting mainly opaque capsules has a central axis which is deviated from the axis of rotation of each capsule.

13. The apparatus of claim 9, wherein said second optical inspecting member for inspecting mainly transparent capsules has a central axis which is positioned in a place passing through the axis of rotation of each capsule.

14. The apparatus of claim 9, wherein:
said first optical inspecting member comprises an illuminating system for illumination, from a predetermined direction, capsules; each capsule having a cap portion and a body portion both or either of which is transparent or opaque, said capsules being carried in a lengthwise direction thereof which being rotated about a lengthwise axis thereof; and a photoelectric converter for receiving a diffused reflective light from said capsules; and
said second optical inspecting member comprises an illuminating system for illuminating said capsules, with a direction perpendicular to said lengthwise axis taken as its optic axis; and a photoelectric converter, placed on said optic axis, for receiving a specularly reflective light from said capsules;
said first and second optical inspecting members being disposed in a predetermined locational relation in a conveying direction of said capsules, whereby the sorting of said capsules and the inspection of their opaque portions are carried out by said first optical inspecting member and the inspection of their transparent portions is carried out by said second optical inspecting member in order to accomplish inspection of said capsules in accordance with their type.

* * * * *

UNITED STATES PATENT AND TRADEMARK OFFICE
CERTIFICATE OF CORRECTION

PATENT NO. : 4,593,190
DATED : June 3, 1986
INVENTOR(S) : Tetsuji KAWASAKI et al It is certified that error appears in the above-identified patent and that said Letters Patent is hereby corrected as shown below:

COLUMN 3, line 17, "are" should be deleted;

COLUMN 5, lines 47-48, "inspeciton" should read --inspection--;

COLUMN 5, line 48, "inspection" should read --inspecting--

COLUMN 12, (claim 14), line 32, "which" should read --while--.

Signed and Sealed this

First Day of September, 1987

*Attest:*

DONALD J. QUIGG

*Attesting Officer*  *Commissioner of Patents and Trademarks*